United States Patent [19]
Hunt et al.

[11] Patent Number: 4,639,433
[45] Date of Patent: Jan. 27, 1987

[54] GLYCOPEPTIDE DERIVATIVES

[75] Inventors: Ann H. Hunt, Greenwood; R. Michael Molloy, Danville; Ramakrishnan Nagarajan; Amelia A. Schabel, both of Indianapolis, all of Ind.

[73] Assignee: Eli Lilly and Company, Indianapolis, Ind.

[21] Appl. No.: 765,430

[22] Filed: Aug. 14, 1985

[51] Int. Cl.$^4$ .................. A61K 37/00; C07K 9/00
[52] U.S. Cl. ................................ 514/8; 530/322
[58] Field of Search ........................ 514/8; 530/322

[56]         References Cited
         U.S. PATENT DOCUMENTS

| | | | |
|---|---|---|---|
| 3,067,099 | 12/1962 | McCormick et al. | 167/65 |
| 4,495,179 | 1/1985 | Hoehn et al. | 514/9 |
| 4,497,802 | 2/1985 | Debono | 514/8 |
| 4,547,488 | 10/1985 | Merkel | 514/10 |
| 4,548,925 | 10/1985 | Higgins, Jr. et al. | 514/10 |

OTHER PUBLICATIONS

Harris et al., "Structure of the Glycopeptide Antibiotic Vancomycin. Evidence for an Asparagine Residue in the Peptide", *J. Am. Chem. Soc.* 104, 4293-4295, (1982).

Pfeiffer, "Structual Features of Vancomycin", Reviews of Infectious Diseases, vol. 3, Suppl., S205-S209, (Nov.-Dec. 1981).

Perkins, "Specificity of Combination between Mucopeptide Precursors and Vancomycin or Ristocetin", *Biochem. J.* 111, 195-205, (1969).

Derwent Abstract No. 84 160164/26 (Eli Lilly and Company) of European Pat. No. 112-184-A, (Jun. 27, 1984).

*Primary Examiner*—Delbert R. Phillips
*Attorney, Agent, or Firm*—Nancy J. Harrison

[57]            ABSTRACT

Novel glycopeptide derivatives of formula 1 and methods for their preparation from the glycopeptide antibiotics vancomycin, A51568A, A51568B, M43A and M43D, are provided. The new glycopeptide derivatives are useful antibacterial agents.

29 Claims, No Drawings
}

GLYCOPEPTIDE DERIVATIVES

SUMMARY OF THE INVENTION

This invention relates to new glycopeptide derivatives of formula 1:

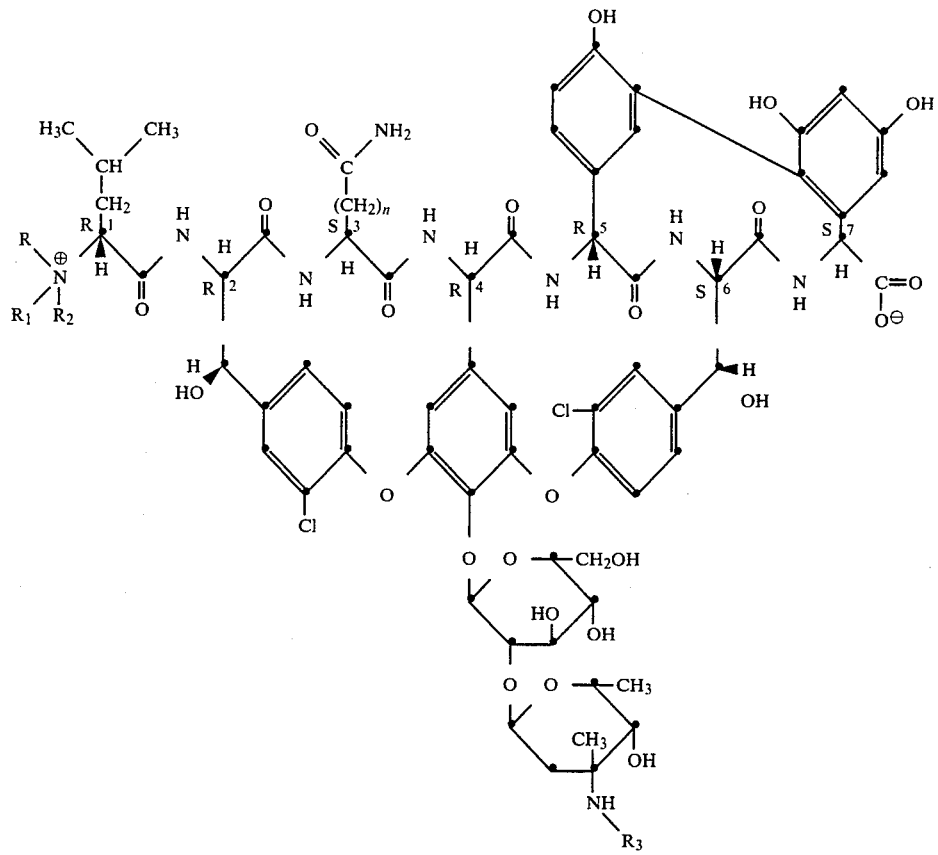

wherein
R and $R_1$ are hydrogen or methyl;
$R_2$ is methyl or $R_3$;
$R_3$ is hydrogen, $C_4$–$C_{24}$-alkanoyl, $C_4$–$C_{24}$-alkenoyl or a $C_4$–$C_{24}$-alkanoyl or $C_4$–$C_{24}$-alkenoyl group which has one or more halo, $C_1$–$C_8$alkoxy, $C_1$–$C_8$-alkylthio, $C_1C_4$-alkoxy-carbonyl, $C_1$–$C_4$-alkanoyl, carboxy, hydroxy, or

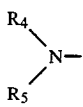

substituents;
$R_4$ and $R_5$ are independently hydrogen or $C_1$–$C_4$-alkyl, or
$R_4$ is hydrogen and $R_5$ is an amino-protecting group; and
n is 1 or 2;
provided that: (1) at least one of $R_2$ and $R_3$ must be other than hydrogen; and (2) when n is 2, R and $R_1$ must be hydrogen; and to the salts of these compounds.

The formula 1 compounds have excellent antibacterial activity, especially against Gram-positive microorganisms. Thus, useful compositions containing the formula 1 compounds and methods of treating infections using the formula 1 compounds are also aspects of this invention.

DETAILED DESCRIPTION

This invention relates to new N-acyl glycopeptide derivatives having formula 1 and to methods for preparing these derivatives. The formula 1 compounds have useful antibacterial activity.

New, improved antibiotics are continually in demand, particularly for the treatment of human diseases. Increased potency, expanded spectrum of bacterial inhibition, increased in vivo efficacy, and improved pharmaceutical properties (such as greater oral absorption, higher blood or tissue concentrations, longer in vivo half life, and more advantageous rate or route of excretion and rate or pattern of metabolism) are some of the goals for improved antibiotics.

In the search for new antibiotics, structural modification of known antibiotics is attempted whenever possible. Many antibiotics, including the glycopeptides, however, have such complex structures that even small changes are difficult to make. Furthermore, it is difficult to predict the effect these changes will make in the activity. Processes for modifying known antibiotics and the new active derivatives made by such processes, therefore, continue to be of great importance.

The formula 1 compounds are new members of the glycopeptide group of antibiotics. The compounds are prepared from the known glycopeptides vancomycin (see, for example, U.S. Pat. No. 3,067,099), antibiotic A51568 factor A (see U.S. Pat. No. 4,495,179) and A51568 factor B (see the copending application of L. D. Boeck, M. M. Hoehn and G. G. Marconi, Ser. No.

561,008, filed Dec. 13, 1983); antibiotic M43A (see the copending application of Harvey M. Higgins, Mack H. McCormick and Kurt E. Merkel, Ser. No. 600,729, filed Apr. 16, 1984), and antibiotic M43D (see the copending application of Kurt E. Merkel, Ser. No. 600,725, filed Apr. 16, 1984). The structural formulas of these glycopeptide antibiotics are shown in formulas 2-6 which follow:

amino group during the acylation reaction. Such groups are well recognized, and selecting a suitable group for this purpose will be apparent (see, for example, "Protective Groups in Organic Chemistry", M. McOmie, Ed, Plenum Press, New York 1973). The tertbutoxycarbonyl (tBOC) and carbobenzyloxy (Cbz) groups are examples of suitable amino-protecting groups.

The formula 1 compounds are shown as zwitterions.

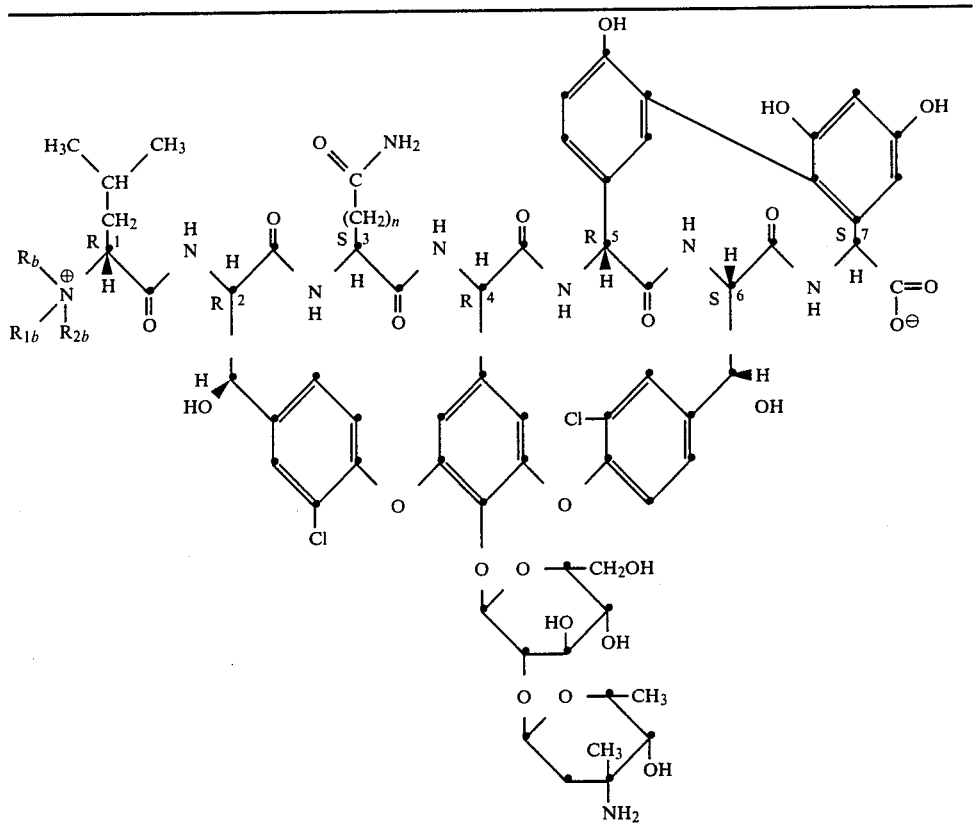

| Compound No. | Compound | $R_b$ | $R_{1b}$ | $R_{2b}$ | n |
|---|---|---|---|---|---|
| 2 | Vancomycin | $CH_3$ | H | H | 1 |
| 3 | M43A | $CH_3$ | $CH_3$ | $CH_3$ | 1 |
| 4 | M43D | $CH_3$ | $CH_3$ | H | 1 |
| 5 | A51568A | H | H | H | 1 |
| 6 | A51568B | H | H | H | 2 |

It will be appreciated that the sugar groups in formulas 1 and 3-6 have the same configuration as do those in vancomycin, i.e., α-O-vancosaminyl-β-O-glucosyl.

As used herein, the terms "alkanoyl" and "alkenoyl" refer to

groups wherein $R_6$ is a $C_3$-$C_{23}$alkyl or $C_3$-$C_{23}$-alkenyl group. The terms "alkyl", "alkoxy", "alkylthio" and "alkenyl" refer to both straight, branched or cyclic hydrocarbon chains. The term "alkenyl" refers to an unsaturated group containing not more than three double bonds. The double bonds of the alkenyl group may be either in the cis or trans configuration.

The term "halo" refers to chloro, bromo, fluoro or iodo.

The term "amino-protecting group" refers to those groups known in the art to be suitable for protecting the Those in the art will recognize, however, that each has groups which can react to form various salts. All such forms of the formula 1 compounds are part of this invention. The salts are useful, for example, for separating and purifying the antibiotics. In addition, the salts have an improved solubility in water.

The formula 1 salts are prepared using standard procedures for salt preparation. For example, the zwitterion can be neutralized with an appropriate acid to form an acid addition salt.

The formula 1 acid addition salts are particularly useful. Representative suitable salts include those salts formed by standard reactions with both organic and inorganic acids such as, for example, sulfuric, hydrochloric, phosphoric, acetic, succinic, citric, lactic, maleic, fumaric, cholic, pamoic, mucic, D-glutamic, d-camphoric, glutaric, glycolic, phthalic, tartaric, formic, lauric, stearic, salicylic, methanesulfonic, benzenesulfonic, sorbic, picric, benzoic, cinnamic and like acids.

Pharmaceutically acceptable acid addition salts of the formula 1 compounds are an especially preferred group of salts of this invention.

The formula 1 compounds are prepared from the glycopeptide antibiotics vancomycin, A51568A, A51568B, M43A and M43D by reacting the antibiotic a) at the amino group of the sugar vancosamine; b) at the amino group of the leucine moiety; or at both (a) and (b) with the appropriate alkanoyl or alkenoyl side chain using methods conventional in the art of forming an amide bond. The acylation is accomplished, in general, by reacting the antibiotic with an activated derivative of the alkanoic acid or alkenoic acid ($R_6CO_2H$) corresponding to the desired acyl side chain group ($R_6CO-$) wherein $R_6$ is as defined, supra.

The term "activated derivative" means a derivative which renders the carboxyl function of the acylating agent reactive to coupling with the amino group to form the amide bond. Those in the art will recognize suitable activated derivatives, methods for preparing them and methods for using them as acylating agents. Preferred activated derivatives are: (a) an acid halide (e.g. acid chloride), (b) an acid anhydride (e.g. a alkoxyformic acid anhydride) or (c) an activated ester (e.g. a 2,4,5-trichlorophenyl ester). Other methods for activating the carboxyl function include reaction of the carboxylic acid with a carbonyldiimide (e.g. 1,3-dicyclohexylcarbodiimide or 1,3'-diisopropylcarbodiimide) to give a reactive intermediate which, because of instability, is not isolated, the reaction with the amine being carried out in situ.

A preferred method for preparing the compounds of formula 1 is by the active ester method. The use of the 2,4,5-trichlorophenyl ester of the desired alkanoic or alkenoic acid as the acylating agent is most preferred. In this method, an excess amount of the active ester is reacted with the parent antibiotic at room temperature in a non-reactive organic solvent such as N,N-dimethylformamide (DMF). The reaction time is not critical, although a time of about 6 to about 20 hours is preferred. At the conclusion of the reaction, the solvent is removed, and the residue is purified, for example, by reversed phase HPLC using LP-1/C18 as the stationary/phase and a mixture of $H_2O/CH_3CN$ as the solvent system.

The alkanoic and alkenoic acids used as starting materials for the acylation reaction, and their activated derivatives (in particular, the acid chlorides and the 2,4,6-trichlorophenyl esters), are known compounds or can be prepared from known compounds by known methods. The 2,4,5-trichlorophenyl esters are conveniently made by treating the acid chloride of the alkanoic or alkenoic acid with 2,4,5-trichlorophenol in the presence of pyridine or by treating the free alkanoic or alkenoic acid with 2,4,5-trichlorophenol in the presence of 1,3-dicyclohexylcarbodiimide used as a coupling agent. The 2,4,5-trichlorophenyl ester derivatives can be purified, for example, by column chromatography over silica gel in toluene.

In subgeneric aspects, the following formula 1 compounds are preferred embodiments of this invention:

1a. Compounds The compounds wherein $R_2$ is hydrogen and $R_3$ is an acyl group.

1b. Compounds The compounds wherein $R_3$ is hydrogen and $R_2$ is an acyl group.

In addition, of special interest are those 1a and 1b compounds wherein (1) $R_2$ or $R_3 = C_6-C_{16}$-alkanoyl or $C_6-C_{16}$-alkenoyl;

(2) $R_2$ or $R_3 =$

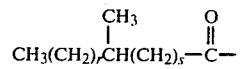

wherein r and s are each, independently, an integer from 0 to 20, provided that r+s must be no less than 3 and no greater than 20;

(3) $R_2$ or $R_3 =$ alkenyl containing one cis or trans double bond;

(4) $R_2$ or $R_3 = C_8-C_{12}$-alkanoyl or $C_8-C_{12}$-alkenoyl;

(5) R=methyl; $R_1$ and $R_2 =$ hydrogen;

(6) R, $R_1$ and $R_2 =$ methyl; and (7) R, $R_1$ and $R_2 =$ hydrogen.

Illustrative compounds of this invention are listed in Table I.

TABLE I

Illustrative Formula 1 Compounds[a]

| Compound No. | R | $R_1$ | $R_2$ | $R_3$ |
|---|---|---|---|---|
| 1 | Me | H | H | 1-oxo-n-butyl |
| 2 | Me | H | H | 1-oxo-n-hexyl |
| 3 | Me | H | H | 1-oxo-n-octyl |
| 4 | Me | H | 1-oxo-n-octyl | H |
| 5 | Me | H | 1-oxo-n-octyl | 1-oxo-n-octyl |
| 6 | Me | H | H | 1-oxo-n-decyl |
| 7 | Me | H | 1-oxo-n-decyl | H |
| 8 | Me | H | 1-oxo-n-decyl | 1-oxo-n-decyl |
| 9 | Me | H | H | 1-oxo-n-dec-10-enyl |
| 10 | Me | H | 1-oxo-n-undec-10-enyl | H |
| 11 | Me | H | 1-oxo-n-dec-10-enyl | 1-oxo-n-dec-10-enyl |
| 12 | Me | H | H | 1-oxo-n-dodecyl |
| 13 | Me | H | 1-oxo-n-dodecyl | H |
| 14 | Me | H | H | 1-oxo-n-tetradecyl |
| 15 | H | H | H | 1-oxo-n-decyl |
| 16 | Me | Me | H | 1-oxo-n-decyl |
| 17 | Me | Me | Me | 1-oxo-n-decyl |
| 18 | Me | H | H | 5-bromo-1-oxo-n-pentyl |
| 19 | Me | H | H | 4-methoxy-1-oxo-n-decyl |
| 20 | Me | H | H | 4-(n-octyloxy)-1-oxo-n-hexyl |
| 21 | Me | H | 4-(n-octyloxy)-1-oxo-n-hexyl | H |
| 22 | Me | H | H | 2-ethyl-1-oxo-butyl |
| 23 | Me | H | H | 3-methyl-1-oxo-propyl |
| 24 | Me | H | H | 4-(methoxycarbonyl)-1-oxo-n-butyl |
| 25 | Me | H | H | 5-hydroxy-1-oxo-n-heptyl |
| 26 | Me | Me | Me | 8-methyl-1-oxo-n-decyl |
| 27 | Me | H | H | 10-methyl-1-oxo-n-undecyl |
| 28 | Me | H | H | 10-methyl-1-oxo-n-dodecyl |
| 29 | Me | H | 8-methyl-1-oxo-n-decyl | H |
| 30 | Me | H | 5-bromo-1-oxo-n-pentyl | H |
| 31 | Me | H | 3-methyl-1-oxo-propyl | H |
| 32 | Me | H | H | 2-[N—(Cbz)amino]-1-oxo-isopentyl |
| 33 | Me | H | H | 2-amino-1-oxo-isopentyl |
| 34 | Me | H | H | 1-oxo-isopentyl |
| 35 | Me | H | H | 6-bromo-1-oxo-n-hexyl |
| 36 | Me | H | H | 3-acetyl-1-oxo-n-propyl |

The formula 1 compounds inhibit the growth of a broad spectrum of pathogenic bacteria, especially Gram-positive bacteria. Table 11 summarizes the minimal inhibitory concentrations (MIC's) at which the compounds inhibit certain organisms, as determined by standard agar-dilution assays.

Pharmaceutical formulations of formula 1 compounds and their pharmaceutically acceptable salts are also part of this invention. Thus, a formula 1 compound, preferably as a pharmaceutically acceptable salt, can be

TABLE II

In Vitro Activity of Formula 1 Compounds

| | MIC (mcg/ml) Compound Number[a] | | | | | | | | | |
|---|---|---|---|---|---|---|---|---|---|---|
| Organism | 1 | 2 | 3 | 4 | 5 | 6 | 8 | 9 | 10 | 11 |
| *Staphylococcus aureus* NRRL B313 | 2 | 2 | 1 | 8 | 32 | 0.5 | 2 | 0.5 | 4 | 8 |
| *Staphylococcus aureus* V41 | 2 | 4 | 2 | 8 | 32 | 0.5 | 4 | 0.5 | 4 | 8 |
| *Staphylococcus aureus* X400 | 2 | 4 | 2 | 8 | 32 | 0.5 | 4 | 0.5 | 4 | 16 |
| *Staphylococcus aureus* S13E | 2 | 4 | 2 | 8 | 32 | 0.5 | 8 | 0.5 | 4 | 8 |
| *Staphylococcus epidermidis* EPI1 | 8 | 16 | 8 | 32 | — | 2 | 32 | 2 | 32 | 64 |
| *Staphylococcus epidermidis* 222 | 4 | 8 | 2 | 16 | 64 | 1 | 8 | 0.5 | 8 | 16 |
| *Streptococcus pyogenes* C203 | 1 | 2 | 0.5 | 4 | 32 | 0.5 | 4 | 0.25 | 1 | 2 |
| *Streptococcus pneumoniae* Park 1 | 1 | 2 | 0.5 | 2 | 32 | 1 | 16 | 0.25 | 2 | 4 |
| *Streptococcus faecium* ATCC 9790 | 2 | 4 | 2 | 8 | 32 | 0.5 | 8 | 0.25 | 2 | 8 |
| Streptococcus sp. group D 2041 | 8 | 16 | 4 | 16 | 32 | 1 | 8 | 1 | 4 | 16 |
| *Haemophilus influenzae* C.L. | —[b] | — | — | — | — | — | — | — | — | 32 |
| *Haemophilus influenzae* 76 | — | 128 | — | — | — | — | — | 128 | — | 32 |
| *Escherichia coli* N10 | — | — | — | — | — | — | — | — | — | 128 |
| *Escherichia coli* EC14 | — | — | — | — | — | — | — | — | — | 128 |
| *Escherichia coli* TEM | — | — | — | — | — | — | — | — | — | 64 |
| *Klebsiella pneumoniae* X26 | — | — | — | — | — | — | — | — | — | 128 |
| *Klebsiella pneumoniae* X68 | — | — | — | — | — | — | — | — | — | 128 |
| *Klebsiella pneumoniae* KAE | — | — | — | — | — | — | — | — | — | 128 |

| | MIC (mcg/ml) Compound Number[a] | | | | | | | |
|---|---|---|---|---|---|---|---|---|
| Organism | 12 | 13 | 14 | 22 | 32 | 33 | 34 | 35 | 36 |
| *Staphylococcus aureus* NRRL B313 | 0.25 | 8 | 2 | 2 | 4 | 8 | 2 | 2 | 2 |
| *Staphylococcus aureus* V41 | 0.25 | 8 | 2 | 2 | 4 | 8 | 2 | 2 | 2 |
| *Staphylococcus aureus* X400 | 0.5 | 8 | 2 | 2 | 8 | 32 | 2 | 4 | 2 |
| *Staphylococcus aureus* S13E | 0.5 | 8 | 0.5 | 2 | 4 | 8 | 2 | 2 | 4 |
| *Staphylococcus epidermidis* EPI1 | 2 | 32 | 8 | 8 | 32 | 32 | 8 | 8 | 16 |
| *Staphylococcus epidermidis* 222 | 0.5 | 8 | 2 | 2 | 8 | 32 | 4 | 4 | 4 |
| *Streptococcus pyogenes* C203 | 0.5 | 8 | 2 | 2 | 2 | 8 | 1 | 2 | 1 |
| *Streptococcus pneumoniae* Park 1 | 0.5 | 8 | 2 | 2 | 2 | 8 | 1 | 1 | 1 |
| *Streptococcus faecium* ATCC 9790 | 0.5 | 8 | 0.5 | 2 | 4 | 8 | 2 | 2 | 4 |
| Streptococcus sp. group D 2041 | 0.5 | 8 | 0.5 | 8 | 8 | 32 | 8 | 8 | 8 |
| *Haemophilus influenzae* C.L. | — | 128 | 128 | 128 | 128 | — | — | — | — |
| *Haemophilus influenzae* 76 | — | 32 | 128 | 128 | 128 | — | — | — | — |
| *Escherichia coli* N10 | — | — | — | — | — | — | — | — | — |
| *Escherichia coli* EC14 | — | — | — | — | — | — | — | — | — |
| *Escherichia coli* TEM | — | — | — | — | — | — | — | — | — |
| *Klebsiella pneumoniae* X26 | — | — | — | — | — | — | — | — | — |
| *Klebsiella pneumoniae* X68 | — | — | — | — | — | — | — | — | — |
| *Klebsiella pneumoniae* KAE | — | — | — | — | — | — | — | — | — |

[a]Compound numbers from Table I
[b]— = not active at 128 mcg/ml

Some of the compounds of this invention have also shown in vivo antimicrobial activity against experimental bacterial infections. When two doses of test compound were administered to mice in experimental infections, the activity observed was measured as an $ED_{50}$ value [effective dose in mg/kg to protect 50% of the test animals: see Warren Wick, et al., J. Bacteriol. 81, 233–235 (1961)]. $ED_{50}$ values observed are given in Table III.

TABLE III $ED_{50}$ Values for Formula 1 Compounds[a,b]

| | $ED_{50}$ (mg/kg/2) Compound Numbers | | | | | | | |
|---|---|---|---|---|---|---|---|---|
| Organism | 1 | 2 | 3 | 6 | 9 | 12 | 14 | vancomycin |
| *Staphylococcus aureus* | 6.3 | 11.2 | 6.9 | 5 | 3.7 | 6.8 | 6.6 | 1.8–3.7 |
| *Streptococcus pyogenes* | 5.5 | 12.9 | 4.4 | 2.9 | 1.9 | 1.6 | 1.4 | 0.99–1.1 |
| *Streptococcus pneumoniae* | 3.6 | 3.5 | 4.8 | 1.4 | 1.8 | 0.9 | 1.3 | 0.90–0.93 |

[a]Administered subcutaneously
[b]Compound numbers from Table I formulated for oral or parenteral administration for the therapeutic or prophylactic treatment of bacterial infections. For example, the compound can be admixed with conventional pharmaceutical carriers and excipients and used in the form of tablets, capsules, elixirs, suspensions, syrups, wafers and the like.

The compositions comprising a formula 1 compound will contain from about 0.1 to about 90% by weight of the active compound, and more generally from about 10 to about 30%.

The compositions may contain common carriers and excipients, such as corn starch or gelatin, lactose, sucrose, microcrystalline cellulose, kaolin, mannitol, dicalcium phosphate, sodium chloride and alginic acid.

Disintegrators commonly used in the formulations of this invention include croscarmellose sodium, microcrystalline cellulose, corn starch, sodium starch glycolate and alginic acid.

Tablet binders that can be included are acacia, methylcellulose, sodium carboxymethylcellulose, polyvinylpyrrolidone (Povidone), hydroxypropyl methylcellulose, sucrose, starch and ethylcellulose.

Lubricants that can be used include magnesium stearate or other metallic stearates, stearic acid, silicone fluid, talc, waxes, oils and colloidal silica.

Flavoring agents such as peppermint, oil of wintergreen, cherry flavoring or the like can also be used.

It may be desirable to add a coloring agent to make the dosage form more esthetic in appearance or to help identify the product.

For intravenous (IV) use, a water soluble form of the antibiotic can be dissolved in one of the commonly used intravenous fluids and administered by infusion. such fluids as, for example, physiological saline, Ringer's solution or 5% dextrose solution can be used.

For intramuscular preparations, a sterile formulation of a suitable soluble form of the compound, for example the hydrochloride salt form, can be dissolved and administered in a pharmaceutical diluent such as Water-for-Injection, physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

For oral use, a sterile formulation of a suitable form of the antibiotic, for example the hydrochloride salt form, formulated in a diluent such as distilled or deionized water, is particularly useful.

Alternatively, the unit dosage form of the antibiotic can be a solution of the antibiotic, or a salt thereof, in a suitable diluent in sterile, hermetically sealed ampoules. The concentration of the antibiotic in the unit dosage may vary, e.g. from about 1 percent to about 50 percent depending on the particular form of the antibiotic and its solubility and the dose desired by the physician.

In a further aspect, this invention provides a method for treating susceptible bacterial infections, especially those caused by Gram-positive microorganisms, in animals. The animal may be either susceptible to, or infected with, the microorganism. The method comprises administering to the animal an effective amount of a formula 1 compound or its pharmaceutically acceptable salt. In general, an effective amount of a formula 1 compound is a dose between about 0.5 and about 100 mg/kg. A preferred dose is from about 10 to about 60 mg/kg of active compound. A typical daily dose for an adult human is from about 250 mg to about 1.0 g.

In practicing this method, the antibiotic can be administered in a single daily dose or in multiple doses per day. The treatment regime may require administration over extended periods of time, e.g., for several days or for from two to three weeks. The amount per administered dose or the total amount administered will depend on such factors as the nature and severity of the infection, the age and general health of the patient, the tolerance of the patient to the antibiotic and the microorganism or microorganisms involved in the infection.

A convenient method of practicing the treatment method is to administer the antibiotic via IV infusion. In this procedure a sterile formulation of a suitable soluble salt of the antibiotic is incorporated in a physiological fluid, such as 5% dextrose solution, and the resulting solution is infused slowly IV. Alternatively, the piggy-back method of IV infusion can also be used.

In another embodiment, this invention relates to methods of increasing feed-utilization efficiency in poultry, swine, sheep and cattle, of promoting growth rates in cattle raised for meat production and of enhancing milk production in lactating ruminants. For increasing feed-utilization efficiency and promoting growth, a formula 1 compound is administered orally in a suitable feed in an amount of from about 2 to about 200 grams per ton of total feed. For beef cattle, for example, a range of about 12 to 3000 mg/head/day is suitable. For enhancing milk production in lactating ruminants, oral administration of a daily amount of from about 0.04 to about 16 mg/kg of body weight (or about 25 to about 5000 mg/ruminant/day) is suggested.

The following examples are provided to illustrate this invention. To simplify discussion, "$N^{van}$" is used to indicate the nitrogen on vancosamine and "$N^{leu}$" is used to indicate the nitrogen in the leucine group. Reactions were followed by analytical high performance liquid chromatography (HPLC), using a Water's Bondapak $C_{18}$ column with a gradient solvent system of $CH_3CN$ and 0.5% triethylamine (pH 3) buffer and detecting with UV at 254 nm.

EXAMPLE 1

Preparation of $N^{van}$-(1-oxo-n-Decyl)vancomycin (Compound 6) and
$N^{van},N^{leu}$-di(1-oxo-n-decyl)vancomycin (Compound 8)

Vancomycin free base (4 g, 2.76 mmoles) was dissolved in DMF (150 ml). n-Decanoyl 2,4,5-trichlorophenyl active ester (4 g, 11.39 mmoles) was added. The reaction mixture was stirred at room temperature for two days. The mixture was then transferred to a Virtis jar and mixed with Celite to form a very thick paste. This was dried under vacuum overnight.

The powdery residue obtained was stirred in methanol and filtered. The filtrate was again stirred in methanol and filtered. The methanol filtrates were pooled and evaporated under vacuum to dryness. The residue thus obtained was triturated with $CH_2Cl_2$ and filtered. The insoluble residue was then purified by HPLC, using a Waters Prep Pak/500 column. The column was eluted with an acetonitrile-water system containing 1% pyridinium acetate and was monitored using a UV detector at 280 nm. This separation gave $N^{van}$-(1-oxo-n-decyl)-vancomycin (709.1 mg) and $N^{van}$, $N^{leu}$-di(1-oxo-N-decyl)vancomycin (498.4 mg). The products were confirmed by fast atom bombardment mass spectrometry.

EXAMPLES 2-12

The procedure described in Example 1, but using the appropriate starting active ester, was used to prepare mon-$N_{van}$-, mono-$N_{leu}$- and di-$N_{van}$, $N_{leu}$-acyl derivatives. The reaction time can be shortened to half by increasing the raction temperature to about 65° C.

The following compounds were thus prepared:

| Compound | Name |
| --- | --- |
| 1 | $N^{van}$—(1-oxo-n-butyl)vancomycin |
| 2 | $N^{van}$—(1-oxo-n-hexyl)vancomycin |
| 3 | $N^{van}$—(1-oxo-n-octyl)vancomycin |
| 4 | $N^{leu}$—(1-oxo-n-octyl)vancomycin |
| 5 | $N^{van},N^{leu}$—di(1-oxo-n-octyl)vancomycin |
| 9 | $N^{van}$—(1-oxo-10-n-decenyl)vancomycin |
| 10 | $N^{leu}$—(1-oxo-10-n-decenyl)vancomycin |
| 11 | $N^{van},N^{leu}$—(1-oxo-10-n-decenyl)vancomycin |
| 12 | $N^{van}$—(1-oxo-n-dodecyl)vancomycin |
| 13 | $N^{leu}$—(1-oxo-n-dodecyl)vancomycin |
| 14 | $N^{van}$—(1-oxo-n-tetradecyl)vancomycin |
| 22 | $N^{van}$—(2-ethyl-1-oxo-n-butyl)vancomycin |
| 32 | $N^{van}$—[2-(N—Cbz—amino)-1-oxo-isopentyl]vancomycin |
| 33 | $N^{van}$—(2-amino-1-oxo-isopentyl)vancomycin |
| 34 | $N^{van}$—(1-oxo-isopentyl)vancomycin |
| 35 | $N^{van}$—(6-bromo-n-hexyl)vancomycin |

-continued

| Compound | Name |
|---|---|
| 36 | $N^{van}$—(3-acetyl-1-oxo-n-propyl)vancomycin |

Table IV summarizes certain physical characteristics of the exemplified compounds.

TABLE IV

Physical Characteristics of Formula 1 Compounds[a,b]

| Compound No. | $R_2$ | $R_3$ | HPLC Gradient System[c] | HPLC Retention Time (minutes) | FDMS[d] Parent Ion ($m^+ + 1$) |
|---|---|---|---|---|---|
| 1 | H | $C_3H_7CO$ | C | 16.9 | 1518 |
| 2 | H | $C_5H_{11}CO$ | B | 12.01 | 1546 |
| 3 | H | $C_7H_{15}CO$ | A | 13.9 | 1574 |
| 4 | $C_7H_{15}CO$ | H | A | 15.72 | 1574 |
| 5 | $C_7H_{15}CO$ | $C_7H_{15}CO$ | A | 19.32 | 1699 |
| 6 | H | $C_9H_{19}CO$ | A | 12.4 | 1602 |
| 8 | $C_9H_{19}CO$ | $C_9H_{19}CO$ | A | 20.36 | 1755 |
| 9 | H | $CH_2=CH(CH_2)_8CO$ | A | 12.46 | 1614 |
| 10 | $CH_2=CH(CH_2)_8CO$ | H | A | 14.15 | 1614 |
| 11 | $CH_2=CH(CH_2)_8CO$ | $CH_2=CH(CH_2)_8CO$ | A | 18.22 | |
| 12 | H | $C_{11}H_{23}CO$ | A | 18.94 | 1629 |
| 13 | $C_{11}H_{23}CO$ | H | A | 22.05 | 1629 |
| 14 | H | $C_{13}H_{27}CO$ | A | 21.6 | 1658 |

[a]Compound numbers from Table I
[b]R = Me; $R_1$ = H in exemplified compounds
[c]Water's Bondapak $C_{18}$ Column; UV detection at 254 nm; $CH_3CN$:0.2% triethylamine buffer solvent systems in the following gradients

| System | Gradient |
|---|---|
| A | 5% → 80% |
| B | 10% → 60% |
| C | 5% → 30% |

[d]Field desorption mass spectrometry

EXAMPLES 13–17

Using the procedure described in Example 1 (with the appropriate starting active ester), the following compounds can be prepared:

$N^{van}$-(1-oxo-9,12-octadecenyl)vancomycin
$N^{van}$-(1-oxo-4-pentenyl)vancomycin
$N^{leu}$-(1-oxo-9-octadecenyl)vancomycin
$N^{leu}$-(1-oxo-hexadecyl)vancomycin
$N^{van}$-(1-oxo-9-octadecenyl)vancomycin
$N^{van}$-(1-oxo-2-cyclohexyl-ethyl)vancomycin
$N^{van}$-(3-chloro-1-oxo-n-propyl)-A51568A
$N^{van}$-(1-oxo-n-decyl)-A51568A
$N^{van}$-(5-chloro-1-oxo-n-pentyl)-A51568A
$N^{van}$-(1-oxo-n-octyl)-A51568A
$N^{van}$-(3-cyclopentyl-1-oxo-n-propyl)-A51568B
$N^{van}$-(1-oxo-n-decyl)-A51568B
$N^{leu}$-(1-oxo-n-eicosanyl)-A51568B
$N^{van}$-(1-oxo-n-decyl)-M43D
$N^{van}$-(cycloheptanecarbonyl)-M43D

We claim:
1. compound of the formula:

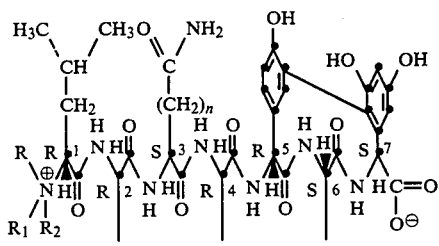
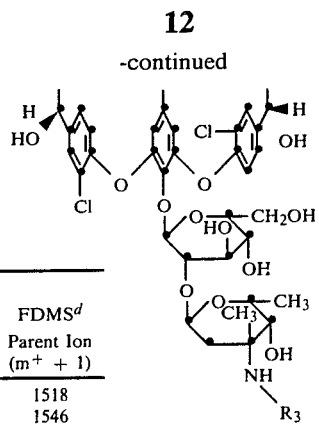

wherein
R and $R_1$ are hydrogen or methyl;
$R_2$ is methyl or $R_3$;
$R_3$ is hydrogen, $C_4$-$C_{24}$-alkanoyl, $C_4$-$C_{24}$-alkenoyl or a $C_4$-$C_{24}$-alkanoyl or $C_4$-$C_{24}$-alkenoyl group which has one or more halo, $C_1$-$C_8$-alkoxy, $C_1$-$C_8$-alkylthio, $C_1$-$C_4$-alkoxycarbonyl, $C_1$-$C_4$-alkanoyl, carboxy, hydroxy, or

substituents;
$R_4$ and $R_5$ are independently hydrogen or $C_1$-$C_4$-alkyl, or
$R_4$ is hydrogen and $R_5$ is an amino-protecting group;
and
n is 1 or 2;
provided that: (1) at least one of $R_2$ and $R_3$ must be other than hydrogen; and (2) when n is 2, R and $R_1$ must be hydrogen; and the salts of these compounds.
2. A compound of claim 1 wherein R is methyl and $R_1$ and $R_2$ are hydrogen.
3. A compound of claim 1 wherein R and $R_1$ are methyl and $R_2$ is hydrogen.

4. A compound of claim 1 wherein R, $R_1$ and $R_2$ are methyl.

5. A compound of claim 1 wherein R, $R_1$ and $R_2$ are hydrogen.

6. A compound of claim 5 wherein n is 1.

7. A compound of claim 5 wherein n is 2.

8. A compound of claim 1 wherein $R_3$ is $C_4$–$C_{24}$-alkanoyl or $C_4$–$C_{24}$-alkenoyl.

9. A compound of claim 1 wherein $R_2$ is $C_4$–$C_{24}$-alkanoyl or $C_4$–$C_{24}$-alkenoyl.

10. A compound of claim 8 wherein $R_3$ is $C_6$–$C_{16}$-alkanoyl or $C_6$–$C_{16}$-alkenoyl.

11. A compound of claim 9 wherein $R_2$ is $C_6$–$C_{16}$-alkanoyl or $C_6$–$C_{16}$-alkenoyl.

12. A compound of claim 10 wherein $R_3$ is decanoyl.

13. A compound of claim 2 wherein $R_3$ is $C_4$–$C_{24}$-alkanoyl or $C_4$–$C_{24}$-alkenoyl.

14. A compound of claim 2 wherein $R_3$ is $C_8$–$C_{16}$-alkanoyl or $C_8$–$C_{16}$-alkenoyl.

15. A compound of claim 14 wherein $R_3$ is decanoyl.

16. The compound of claim 15 wherein $R_3$ is n-decanoyl.

17. A compound of claim 14 wherein $R_3$ is nonanoyl.

18. A compound of claim 14 wherein $R_3$ is undecanoyl.

19. A compound of claim 14 wherein $R_3$ is dodecanoyl.

20. A compound of claim 14 wherein $R_3$ is tetradecanoyl.

21. A compound of claim 1 wherein the salts are pharmaceutically acceptable.

22. A compound of claim 2 wherein the salts are pharmaceutically acceptable.

23. A compound of claim 13 wherein the salts are pharmaceutically acceptable.

24. A composition useful for the control of susceptible bacterial infections comprising an effective amount of a compound of claim 21 and a suitable pharmaceutical vehicle.

25. A composition useful for the control of susceptible bacterial infections comprising an effective amount of a compound of claim 22 and a suitable pharmaceutical vehicle.

26. A composition useful for the control of susceptible bacterial infections comprising an effective amount of a compound of claim 23 and a suitable pharmaceutical vehicle.

27. A method for treating susceptible bacterial infections which comprises administering an effective amount of a composition of claim 24 to an animal.

28. A method for treating susceptible bacterial infections which comprises administering an effective amount of a composition of claim 25 to an animal.

29. A method for treating susceptible bacterial infections which comprises administering an effective amount of a composition of claim 26 to an animal.

* * * * *

UNITED STATES PATENT AND TRADEMARK OFFICE
CERTIFICATE OF CORRECTION

PATENT NO. : 4,639,433          Page 1 of 2
DATED     : January 27, 1987
INVENTOR(S) : Ann H. Hunt, et al.

It is certified that error appears in the above—identified patent and that said Letters Patent is hereby corrected as shown below:

In the structural formulas in columns 1-2, 3-4 and 11-12, the following portions should be corrected:

| | | |
|---|---|---|
|  | should read | 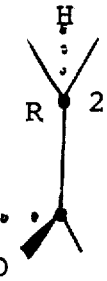 |
| 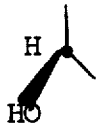 | should read | 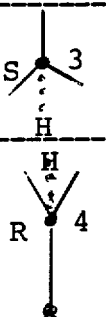 |
|  | should read | 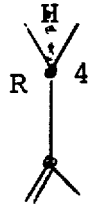 |
| 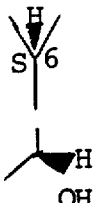 | should read | 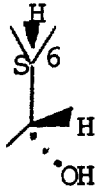 |

UNITED STATES PATENT AND TRADEMARK OFFICE
CERTIFICATE OF CORRECTION

PATENT NO. : 4,639,433

DATED : January 27, 1987

INVENTOR(S) : Ann H. Hunt, et al.

It is certified that error appears in the above-identified patent and that said Letters Patent is hereby corrected as shown below:

[chemical structure with S, H, 7] should read [chemical structure with S, H, 7]

Signed and Sealed this

Nineteenth Day of April, 1988

Attest:

DONALD J. QUIGG

*Attesting Officer*     *Commissioner of Patents and Trademarks*